(12) United States Patent
Worrel

(10) Patent No.: US 10,258,368 B2
(45) Date of Patent: *Apr. 16, 2019

(54) RETRACTABLE CANNULA FOR SURGICAL PROCEDURES

(71) Applicant: Arthroscopic Innovations, LLC, Dallas, TX (US)

(72) Inventor: Daniel A. Worrel, Dallas, TX (US)

(73) Assignee: SUREMKA, LLC, Dallas, TX (US)

(*) Notice: Subject to any disclaimer, the term of this patent is extended or adjusted under 35 U.S.C. 154(b) by 388 days.

This patent is subject to a terminal disclaimer.

(21) Appl. No.: 14/300,755

(22) Filed: Jun. 10, 2014

(65) Prior Publication Data

US 2014/0288377 A1    Sep. 25, 2014

Related U.S. Application Data

(63) Continuation-in-part of application No. 13/626,206, filed on Sep. 25, 2012, now Pat. No. 8,777,902, which
(Continued)

(51) Int. Cl.
*A61B 17/34*    (2006.01)

(52) U.S. Cl.
CPC ...... *A61B 17/3417* (2013.01); *A61B 17/3431* (2013.01); *A61B 2017/3456* (2013.01); *A61B 2017/3484* (2013.01)

(58) Field of Classification Search
CPC ............ A61B 17/3417; A61B 17/3415; A61B 17/3431; A61B 2017/348;
(Continued)

(56) References Cited

U.S. PATENT DOCUMENTS

| 3,397,699 A | * | 8/1968 | Kohl | ............... | A61M 25/04 |
| | | | | | 29/451 |
| 5,279,564 A | * | 1/1994 | Taylor | ............... | A61B 17/34 |
| | | | | | 604/104 |

(Continued)

OTHER PUBLICATIONS

International Search Report and Written Opinion for International Patent No. PCT/US2017/038057 filed Jun. 18, 2017; 9 pgs.
(Continued)

*Primary Examiner* — Bhisma Mehta
*Assistant Examiner* — Jenna Zhang
(74) *Attorney, Agent, or Firm* — Hilton IP Law, PLLC; Zachary W. Hilton

(57) ABSTRACT

A cannula assembly having a plurality of outwardly-biased flexible fins capable of inward movement such that the fins converge upon insertion of a trocar device. The fin embodiment including a slot formed therein, with a corresponding raised feature on the trocar shaft capable of engaging the slots. Inward movement of the trocar within the cannula lumen causes the fins to converge. An additional embodiment utilizes outwardly-biased flexible fins that lock together in a closed position, with corrugated features in the fin inner surface that contact the trocar shaft such that, upon insertion of the trocar, the fins unlock and splay outward. One or more of the flexible fins also including one or more penetrations for accepting a biasing device for altering the biasing force of the fin.

9 Claims, 16 Drawing Sheets

Related U.S. Application Data is a continuation of application No. 12/882,030, filed on Sep. 14, 2010, now Pat. No. 8,298,185.

(58) Field of Classification Search
CPC .... A61B 2017/3482; A61B 2017/3484; A61B 2017/3486
See application file for complete search history.

(56) References Cited

U.S. PATENT DOCUMENTS

| | | | | |
|---|---|---|---|---|
| 5,309,894 | A * | 5/1994 | Heckele | A61B 1/303 600/101 |
| 5,391,156 | A | 2/1995 | Hildwein et al. | |
| 5,817,062 | A | 10/1998 | Flom et al. | |
| 5,971,960 | A * | 10/1999 | Flom | A61B 17/3417 604/167.01 |
| 6,228,063 | B1 * | 5/2001 | Aboul-Hosn | A61B 17/3423 604/174 |
| 6,565,536 | B1 * | 5/2003 | Sohn | A61M 25/0074 128/DIG. 26 |
| 6,929,621 | B2 * | 8/2005 | Whitmore | A61M 25/0017 604/109 |
| 8,298,185 | B2 * | 10/2012 | Worrel | A61B 17/3417 604/164.01 |
| 8,679,151 | B2 * | 3/2014 | Rodrigues, Jr. | A61B 17/3423 606/205 |
| 8,777,902 | B2 * | 7/2014 | Worrel | A61B 17/3417 604/164.01 |
| 2006/0129165 | A1 | 6/2006 | Edoga et al. | |
| 2007/0255222 | A1 * | 11/2007 | Li | A61J 15/0015 604/174 |
| 2008/0242930 | A1 * | 10/2008 | Hanypsiak | A61B 17/3421 600/114 |
| 2009/0182288 | A1 | 7/2009 | Spenciner | |
| 2010/0249517 | A1 * | 9/2010 | Fischvogt | A61B 17/3421 600/204 |
| 2011/0034775 | A1 * | 2/2011 | Lozman | A61B 17/1684 600/204 |
| 2011/0092912 | A1 * | 4/2011 | Li | A61J 15/0015 604/175 |
| 2012/0130182 | A1 * | 5/2012 | Rodrigues, Jr. | A61B 17/3423 600/206 |

OTHER PUBLICATIONS

International Search Report and Written Opinion for International Patent No. PCT/US2015/035129 filed Jun. 6, 2015; 5 pgs.
European Search Report and Written Opinion of European Patent Office for European Patent App. No. 15806528.4, dated Nov. 29, 2017; 8 pages.

* cited by examiner

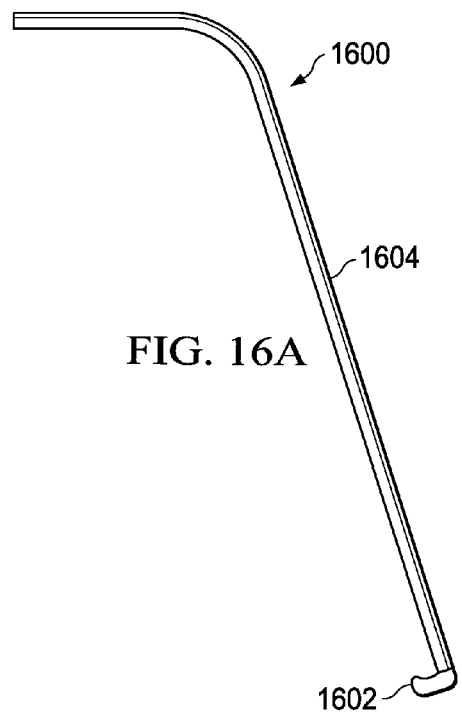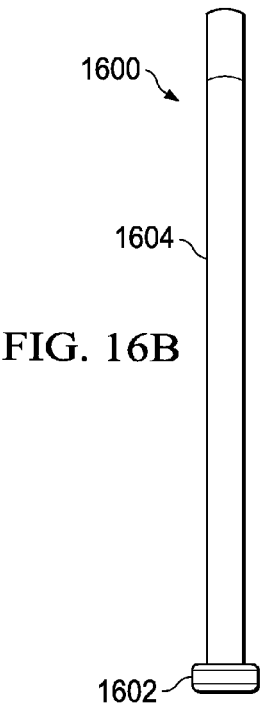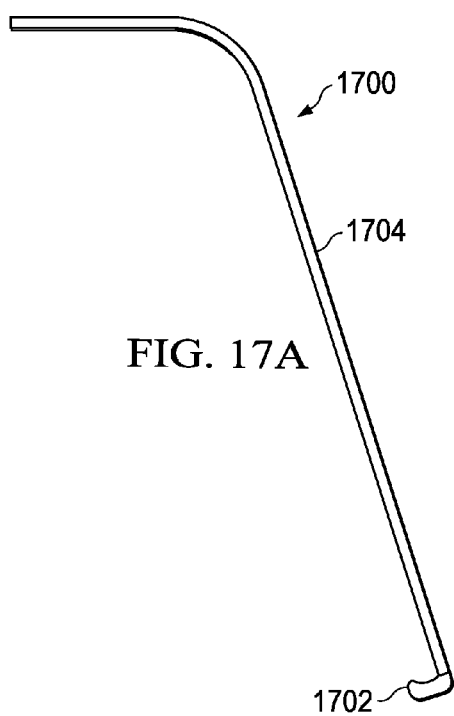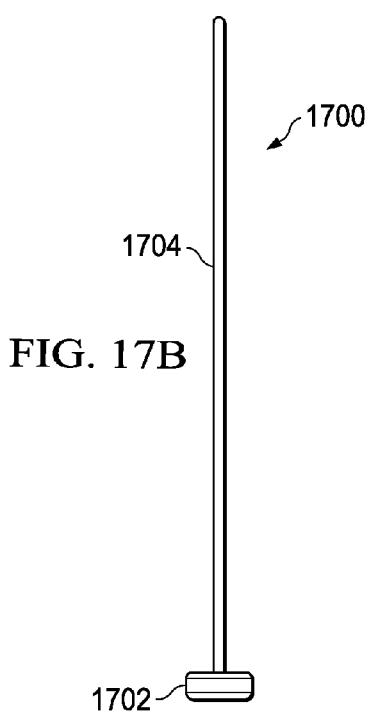

RETRACTABLE CANNULA FOR SURGICAL PROCEDURES

CROSS-REFERENCE TO RELATED APPLICATIONS

This application is a continuation-in-part of prior U.S. patent application Ser. No. 13/626,206, filed on Sep. 25, 2012, which is a continuation of U.S. patent application Ser. No. 12/882,030, filed on Sep. 14, 2010, now U.S. Pat. No. 8,298,185.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to devices for performing percutaneous arthroscopic and other endoscopic surgeries and, more specifically, to surgical cannulae.

2. Description of Related Art Including Information Disclosed Under 37 CFR 1.97 and 1.98

Traditional minimally-invasive arthroscopic surgeries are performed using a cannula device to penetrate small incisions in the patient's skin and outer tissue, creating a port through which surgical tools may be passed to allow access to the underlying structure of interest. For example, in shoulder arthroscopy, the procedure is performed through "portals" in the patient's skin. These portals are formed from small incisions, generally about ½ of an inch to an inch long in the skin, and are located over particular areas of the joint that the surgeon will need to operate upon. Cannulas are then inserted into the portals so that instruments can easily be placed in the shoulder joint. Shoulder arthroscopy itself involves inserting a specially designed video camera with a very bright fiber optic light source into the shoulder joint so that the important parts of the joint can be seen. Instruments that have been specially designed to remove inflamed tissue, attach sutures to bone, and repair torn tendons and ligaments are then used to operate inside the shoulder.

The area between the skin tissue and shoulder joint is quite small. Consequently, it is necessary to "inflate" the area by pumping an irrigation fluid (e.g. saline) into the joint under pressure. In laparoscopic surgical procedures, carbon dioxide in gaseous form may be utilized as an insufflating agent to perform a similar function. The pressure produced by the irrigation fluid pushes the tissue outward from the joint and allows greater room for manipulation of the arthroscopic camera and other surgical tools. However, the actual working angle of the tools is ultimately determined by the length and inner diameter of the cannula. Heavy patients or patients with large amounts of skin and other tissue covering the joint require a longer cannula to penetrate the tissue sufficiently for the procedure. This increased cannula length decreases the working angle of the tools at the joint, limiting the ability of the surgeon to perform the procedure. Although this angle may be improved by increasing the inner diameter of the cannula, there are realistic limits on the useable diameter. For example, the diameter can only be increased by a small amount or else it would effectively eliminate any benefit of conducting the arthroscopic procedure as the portal size could become the equivalent of a large incision as performed in traditional surgery.

Manufacture of cannula devices incorporating shape memory alloys embedded therein can be somewhat costly in practice. Specifically, the molding of shape memory alloys into the polymers of a cannula device can increase the costs associated with the cannula device thereby driving up the overall medical procedure costs. Moreover, disposal and possible recycling of used polymers is readily simple unless non-polymer materials are also present.

What is needed is a cannula device that is capable of compressing the tissue through which it penetrates, that is relatively simple to insert and remove so as to minimize tissue damage to the patient, and that includes a novel means for incorporating a shape memory alloy into its design that is easy to store, use, remove, and reuse. The retractable cannula disclosed herein satisfies these needs and others as will become apparent to one of ordinary skill after a careful study of the detailed description and embodiments.

BRIEF DESCRIPTION OF THE SEVERAL VIEWS OF THE DRAWINGS

The present invention will be more fully understood by reference to the following detailed description of the preferred embodiments of the present invention when read in conjunction with the accompanying drawings, wherein:

FIG. 16A depicts a side view of a rectangular-shaped embodiment of a biasing device;

FIG. 16B depicts a front view of the rectangular-shaped embodiment of a biasing device;

FIG. 17A depicts a side view of a cylindrical-shaped embodiment of a biasing device;

FIG. 17B depicts a front view of the cylindrical-shaped embodiment of a biasing device;

Figure 1:
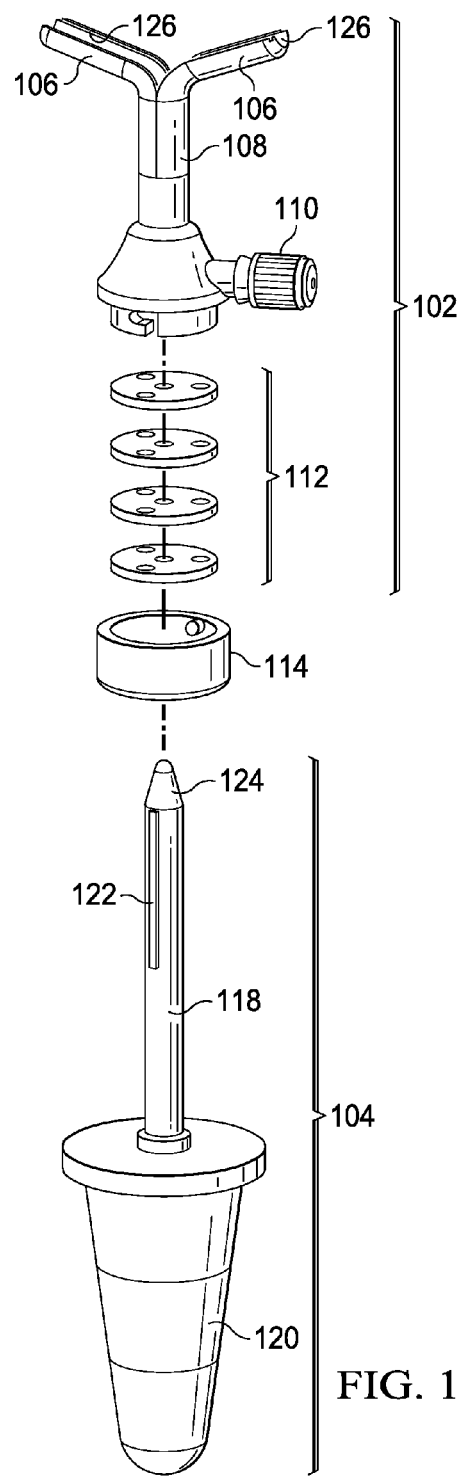
FIG. 1 is an exploded view of a first embodiment of the cannula invention.

The above figures are provided for the purpose of illustration and description only, and are not intended to define the limits of the disclosed invention. Use of the same reference number in multiple figures is intended to designate the same or similar parts. Furthermore, if and when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

FIG. 1 depicts an exploded view of a first embodiment of the cannula invention. As shown in this figure, the complete apparatus includes a cannula device (102) and a trocar device (104). The trocar device (104) includes a handle (120) at its proximal end with a shaft member (118) extending therefrom to form a distal end with a defined tip (124). Along the shaft are multiple raised members (122) that protrude essentially radially from the axial center of the shaft (118) and that extend longitudinally along the shaft length. The raised members (122) in the present embodiment are depicted as extending approximately one half of the length of the shaft (118) near the distal end. However, the length of the raised members (122) may vary in other embodiments. For example, the raised members (122) in another embodiment may be wider than they are in length. Such alternate lengths are within the scope of the present invention. The raised member (122) of the embodiment, as depicted, is also a single element. However, in another embodiment the raised member may be split in two portions such that, on the whole, the raised member (122) may still engage the corresponding slot.

The present embodiment of the cannula device (102) includes body member (108) having a proximal end and a distal end. The body member (108) is essentially cylindrical in shape, having a lumen extending from end to end. Although the body member in the present embodiment is essentially cylindrical in shape, other embodiments may have a geometric cross sectional shape other than circular, or may include a mix of circular and other geometric shape such as a circular lumen cross section with a geometric outer wall cross section or vice versa. The outer wall may also include a ribbed, grooved, or helical raised feature (or even a recessed feature) that assists the device in gripping a patient's skin and muscle tissue for device retention. Such alternate embodiments are envisioned and are within the scope of the present invention.

The proximal end includes a fluid drain port (110) and a proximal collar (114) that retains several silicon discs (112) that are used as fluid seals through which surgical instruments may pass. The proximal collar (114) attaches to the proximal end of the body member for positive retention of the silicon discs (112). The drain port (110) allows for fluid management during surgical procedures in the same fashion as conventional cannula devices.

The distal end of the body member (108) includes a plurality of flexible, yet semi-rigid fins (106) that are formed in the outwardly-biased position (as shown in FIG. 1) during injection molding of the device. The present embodiment utilizes medical grade polymers during the injection molding or extrusion process. These polymers allow the fins to retain the outwardly-biased shape at normal operating temperatures for the device, yet also allow the fins to flex inwardly when sufficient pressure is applied. For example, polyurethanes such as Hytrel® or Arnitel® may be utilized due to the desired durability characteristics, or polyvinyl chloride ("PVC") if expense is a concern.

Figure 3:
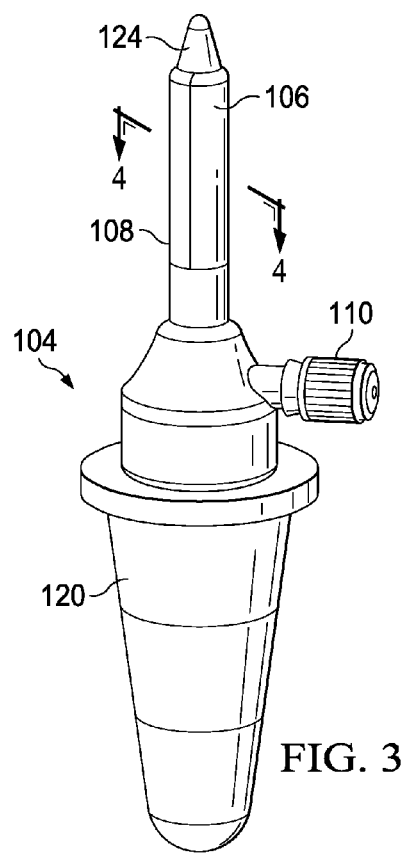
FIG. 3 is an assembled view of the embodiment, highlighting a cross sectional area.

Each fin (106) of the present embodiment includes a radius of curvature that approximates that of the wall of the body member (108) that forms the lumen. When the fins (106) are forcibly moved to the inward position (as depicted in FIG. 3), the inner surface of the fins essentially extends the lumen of the body member (108) to the distal end of the fins. Further, because the fins have a wall thickness, each fin features an edge surface that extends from the fin inner surface to the fin outer surface. It is the edge surface of the fin that contacts the edge surface of the adjacent fin when the fins are in the inward-most position (as in FIG. 3).

Figure 2:
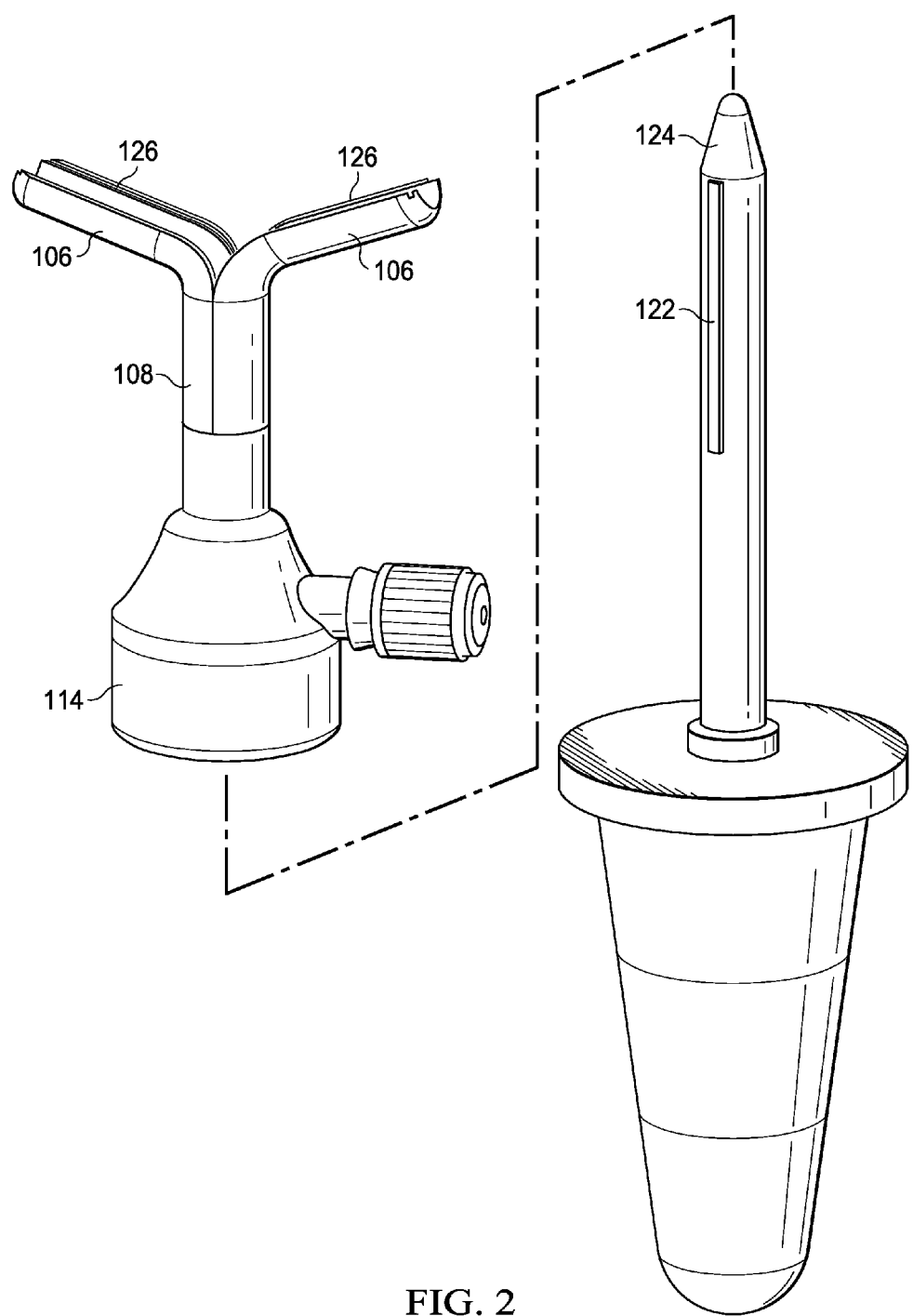
FIG. 2 is a depiction of the cannula invention prior to insertion of the trocar device.

FIG. 2 depicts the cannula invention prior to insertion of the trocar device. As shown, the tip (124) of the trocar device is inserted through the cannula device proximal collar (114) such that the raised members (122) engage with complimentary slots formed within the body member (108) of the cannula device. These complimentary slots extend a distance within the cannula device lumen and along the edge surfaces of the fins (106). This embodiment features two corresponding slots (126), one for each fin. Other embodiments may utilize a greater number of fins and, consequently, would require a correspondingly greater number of slots. For example, an embodiment with three outwardly-biased fins would have three pairs of adjacent fin edge surfaces. Such an embodiment would require three slots within the cannula body member and three corresponding complimentary raised members on the trocar device.

FIG. 3 depicts an assembled view of the embodiment as it would be configured for use once the trocar device (104) is inserted into the cannula device body member (108). As shown, insertion of the trocar device (104) engages the slots within the fins (106), causing the fins (106) to move inward against the outward bias pressure that is normally present. In the full inward position the edge surfaces of the fins (106) meet. This figure also highlights a cross sectional area, which is shown in detail in FIG. 4.

Figure 4:
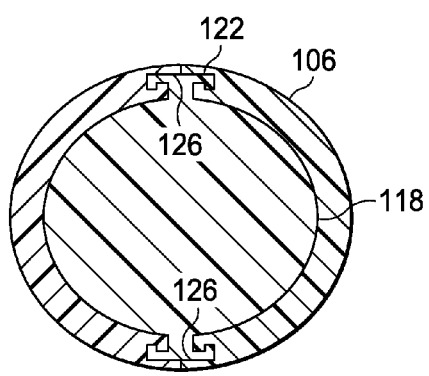
FIG. 4 is a cross section of the working end of the invention as in the assembled view of the embodiment.

The cross section detail depicted in FIG. 4 demonstrates how the trocar shaft member (118) fits within the cannula lumen and engages the complementary slots in the fins (106). In this embodiment, the cannula device has two fins. Formed within the inner wall of the body member are two slots, each having a cross section that resembles a serif font capital letter "T". This slot extends the length of the body member inner wall and is aligned with the origin of the edge surfaces of the fins (106) as they extend from the body member, and accepts a corresponding serif font capital letter "T" shaped raised member (122) on the trocar.

A corresponding portion of the "T" slot is formed in the wall of each fin at the junction of the edge surface and the inner surface. When the fins (106) are in the inward most (or "closed") position (as shown in FIG. 3), the adjoining fin edge surfaces (126) meet and complete the overall "T" slot such that it extends from the body member to the distal end of the fins. Although the corresponding "T" slot portion in the fin edge surfaces (126) extends approximately the entire length of the fin in the present embodiment, other embodiments may extend less than the entire length of the fin.

To prepare the embodiment for use with a patient, the trocar device is inserted into the cannula device lumen such that raised members (122) engage the corresponding and complimentary body member "T" slots. As the trocar shaft (118) is further inserted into the lumen, the raised members slide within the "T" slots until they reach the origin of the edge surfaces of the fins (106). As the trocar is further inserted, the raised members apply stress to the corresponding "tail" elements of "T" slot portions in each fin edge surface (126) causing the fins to move inward and come together along adjacent edge surfaces. This has the effect of "zipping" the fin edges together for insertion of the device into a patient.

Although a serif capital "T" shaped slot cross section is discussed, other embodiments may utilize cross-sectional slot shapes that provide an elemental feature that positively engages and accepts compressive stresses from the corresponding elements of the raised members to cause the fins to move inward and come together along adjacent edge surfaces as the trocar is inserted. Each fin edge surface may include a slot that features a cavity that is larger than the opening formed in the edge surface, with additional material removed from the edge surface where it intersects with the fin inner surface to allow for the corresponding raised member to pass therebetween. For example, the edge surface may have a longitudinal slot formed therein that has a dovetail cross-section. The corresponding raised member would include two corresponding dovetail pin features to engage the adjacent dovetail slots in the adjacent fin edge surfaces. Each fin edge surface may also include a slot with a formed cavity that turns inward towards the inner surface, outward towards the outer surface, or both, such that the slot opening in the edge surface is not aligned with the deepest portion of the slot cavity. For example, the edge surface may have a longitudinal slot that is formed such that cavity beneath the slot opening is centered toward the inner surface and does not share the exact centerline of the cavity opening. Again, the trocar device would include a corresponding raised member that engages the slot as before. In yet another embodiment it is also possible to have a plurality of slots, with each slot having a different geometric cross sectional shape.

Figure 5:
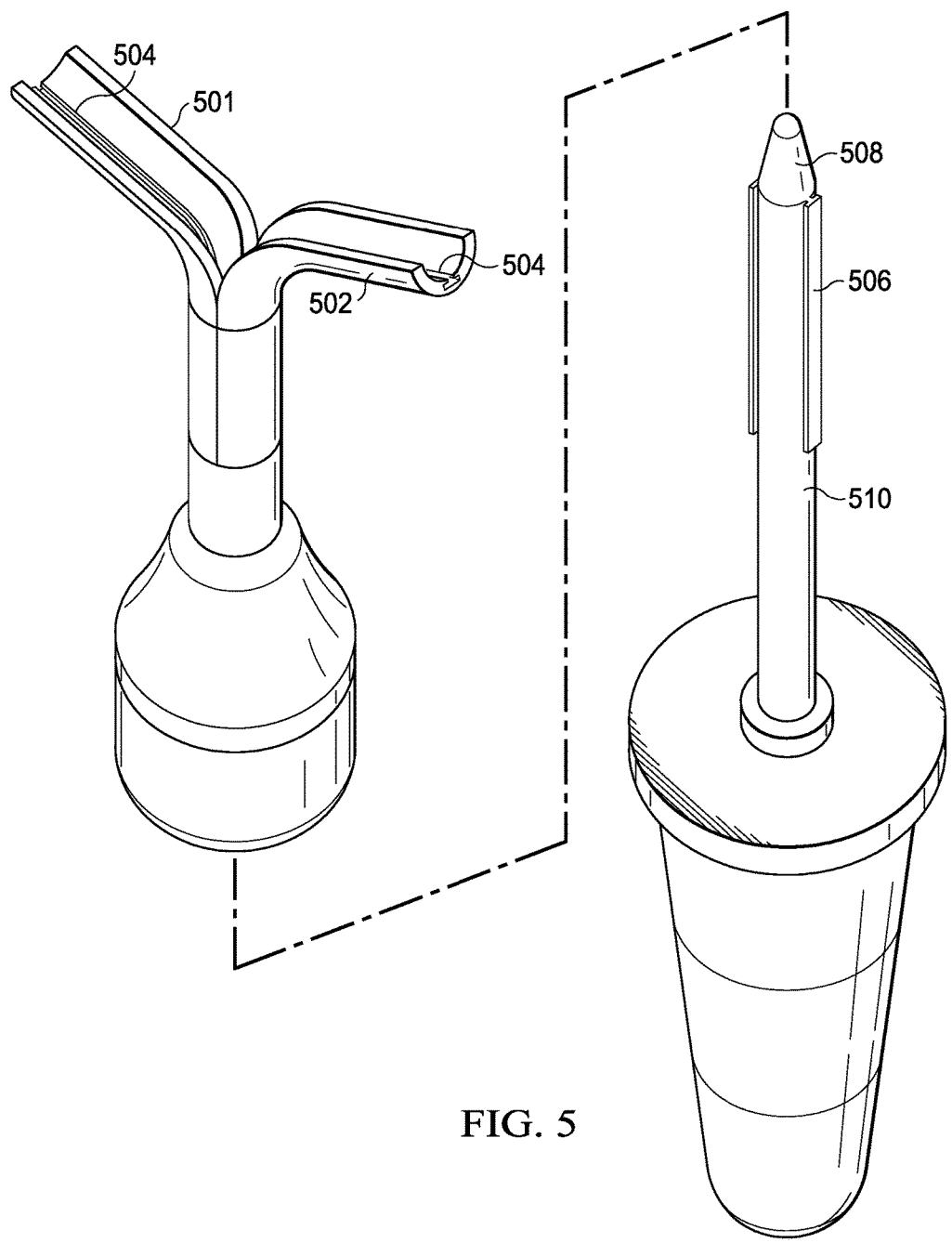
FIG. 5 is a depiction of an alternative embodiment of the cannula invention prior to insertion of the trocar device.
Figure 6:
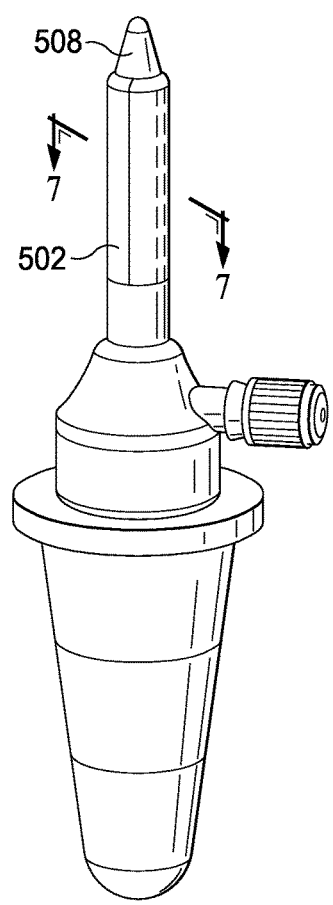
FIG. 6 is an assembled view of the alternative embodiment, highlighting a cross-sectional area.

FIG. 5 depicts an alternative embodiment of the cannula invention prior to insertion of the trocar device. As shown, the trocar device has a shaft member (510) with raised members (506) and a distal tip (508). However, in this embodiment the corresponding slots (504) in the cannula device are formed such that they extend from the proximal opening and along the inner wall of the body member and along the inner wall of the fins (502) at some point between each fin's edge surface (501). Insertion of the trocar device into the cannula device, once again, causes the flexible outwardly-biased fins (502) to move inward such that adjacent fin edge surfaces (501) meet and the closed fins essentially form an extension of the body member as shown in FIG. 6. In this figure, the device is again ready for insertion into a patient.

Figure 8:
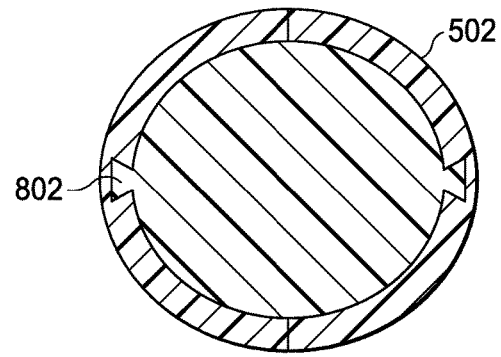
FIG. 8 is a cross section of the working end highlighting an alternative dovetail channel shape.
Figure 9:
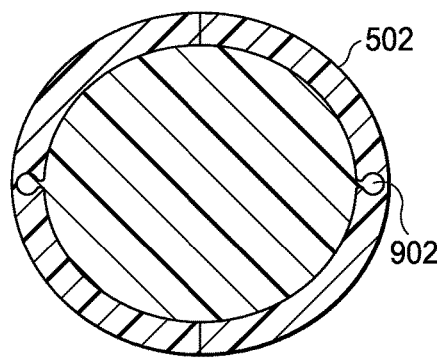
FIG. 9 is a cross section of the working end highlighting an alternative circular channel shape.
Figure 7:
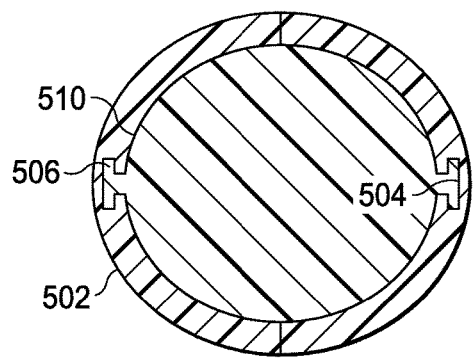
FIG. 7 is a cross section of the working end of the invention as in the assembled view of the alternative embodiment.

FIG. 6 depicts an assembled view of the alternative embodiment, highlighting a cross sectional area. FIG. 7 depicts the cross section of this embodiment in which conventional "T" slots (504) are formed in the fin (502) inner walls approximately midway between the edge surfaces. The trocar shaft (510) features raised members (506) that correspond with each "T" slot. Although the present embodiment depicts a single slot formed midway between the edge surfaces of each fin, other embodiments may utilize multiple slots per fin, with appropriate spacing between the slots. In such embodiments, the trocar shaft will feature corresponding raised members that engage the slots. Further, although the present embodiment describes use of "T" slots in the fins, other geometric slot shapes that afford positive engagement with corresponding raised members may be utilized. For example, FIG. 8 depicts use of dovetail slots (802) formed in the inner surfaces of the fins (502). Likewise, FIG. 9 depicts use of circular slots (902) formed in the inner surfaces of the fins (502). Still other geometric slot shapes are contemplated and are within the scope of the present invention. Further, it is possible to combine fin edge surface slots with inner surface slots. Such an arrangement may be helpful to more evenly distribute the closing forces applied to the fins during insertion of the trocar device and prevent distortion of the fins.

Figure 10:
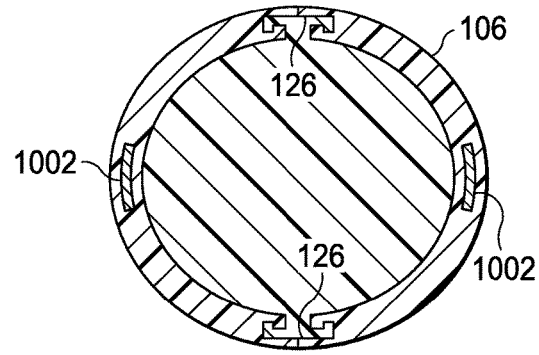
FIG. 10 is a cross section of the working end highlighting an alternative embodiment with an embedded material that assists in the open bias of the fins.
Figure 14:
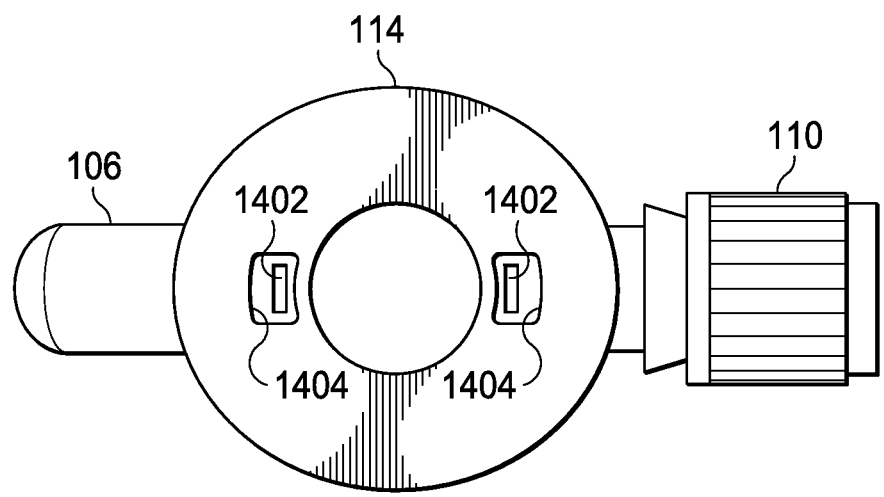
FIG. 14 is a proximal end view depiction of an embodiment of the cannula invention highlighting penetrations into which a biasing device may be inserted.
Figure 15:
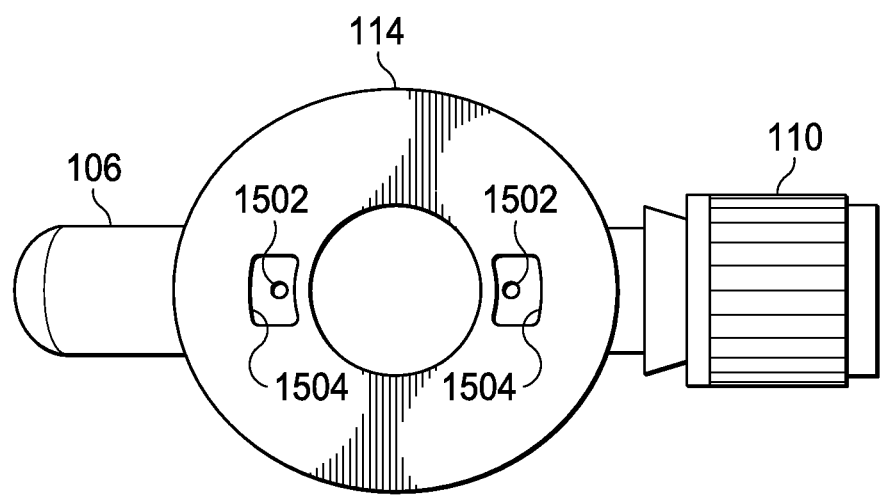
FIG. 15 is a proximal end view depiction of another embodiment of the cannula invention highlighting penetrations into which a biasing device of an alternate shape may be inserted.

In yet another embodiment, it is possible to utilize an embedded shape memory alloy as a biasing device, such as but not limited to Nitinol, in each fin to increase the outward-bias pressure generated by the fins. By increasing the outward bias pressure, it is possible to apply additional compressive stress to the tissue of the patient through which the cannula device is inserted. FIG. 10 depicts such an embodiment. As shown, each fin (106) includes an embedded shape memory alloy strip (1002) within the fin wall at some location between the edge slots (126). This embedded shape memory alloy strip may also be used with the embodiments discussed above, and may be incorporated within the wall beneath or near the respective slot. Further, although the figure depicts use of a single embedded shape memory alloy (1002) in each fin (106), other embodiments may utilize multiple shape memory alloys at various locations spaced within the fin walls. Other biasing devices may include other metals, such as stainless steel, or polymers that exert added biasing force over that provided by the molded fins solely. Moreover, while the shape memory alloys may be permanently included in the fins during manufacture, it is also envisioned that the shape memory alloys may be provided in an insertable/removable form. FIGS. 14 and 15 each present an embodiment of the cannula device incorporating such a feature.

In yet another embodiment it is possible to incorporate an additional alloy with the embedded shape memory alloy to create a bimetallic strip or alter the composition such that it varies, with temperature, the fin outward-bias pressure that is generated. For example, Nitinol may also be "tuned" or "trained" to react at different temperatures by adding additional alloys to its composition. Such a material may be used in the fins of an embodiment to allow the fins to generate greater outward-bias pressures when the fins reach the patient's body temperature.

In other alternate embodiments, integral or removable biasing devices composed of shape memory alloys (such as Nitinol) may be embedded into the fins to generate or supplement outward-bias pressure of varying degrees through electrical activation. For example, a biasing device composed of Nitinol may be embedded into one or more fins of a cannula device and electrically connected to a voltage differential such that the Nitinol forms an electrical circuit. When a current is selectively passed through such circuit, the Nitinol biasing device may be trained to flex outwardly in an amount corresponding to the amount of current passing through such biasing device at least partially forming the aforementioned circuit. A pulse width modulation ("PWM") circuit is preferably utilized to provide for more even heating of the Nitinol biasing device. In this manner, the degree to which the Nitinol biasing device flexes inward and outward may be selectively controlled by the surgical team. Such alternate embodiments configured for electrical activation and in particular, the biasing devices composed of shape memory alloys, should preferably be constructed to include sufficient electrical insulation such that neither the patient nor the surgical team risks being exposed to dangerous electrical current. Electrical components, such as wires, may pass through passages formed in a trocar. Other necessary electrical components needed to provide for electrical activation of such a biasing device (power supply, switch (es), control systems, etc.), may be located remotely from the trocar and cannula or integrated within such structures.

Figure 11:
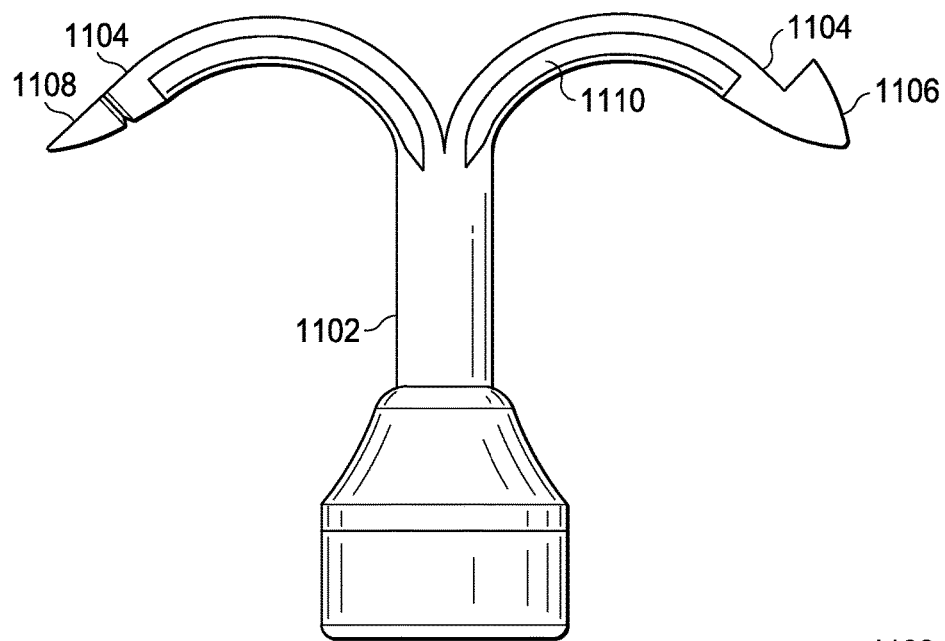
FIG. 11 is an alternative embodiment of the cannula invention with the fins in the open position.

FIG. 11 depicts an alternative embodiment of the cannula device of the present invention. As shown, the cannula device features a body member (1102) with a lumen that exists from the proximal end to the distal end, and a plurality of outwardly-biased fins (1104) extending from the distal end of the body member. Each fin includes a plurality of corrugated features (1110) that extend inward from the outer surface of the fin and are formed along the length of the fin. One fin includes a locking feature (1106) at its distal end for capturing the distal end of the other fins (1108). The locking feature in this embodiment is a conical portion of the distal end of the fin that allows the distal end of the other fins to be captured beneath.

Figure 12:
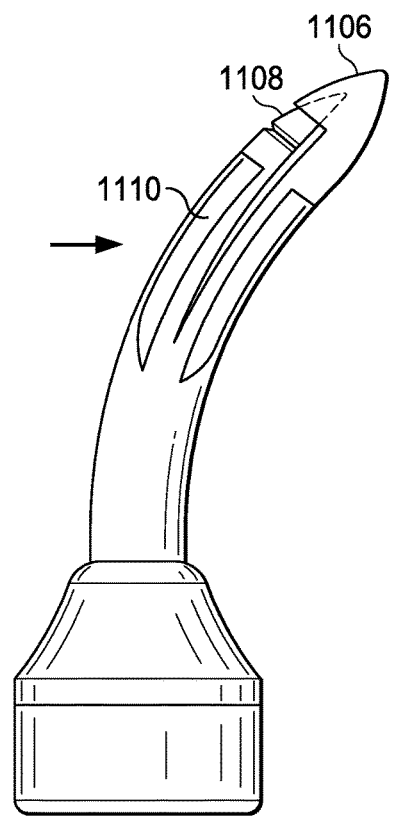
FIG. 12 is a depiction of the process for closing the fins in the alternative embodiment.

This embodiment of the device is prepared as shown in FIG. 12. As depicted, the fins are physically moved inward such that the adjacent fin edges meet and a fin grouping is formed. The fin grouping is then bent toward the fin having the locking feature such that the fin with the locking feature is bent backward as depicted. The relative flexing of the fins in this fashion allows the fins without the locking feature (1108) to be inserted beneath the conical locking feature (1106) such that all are captured in the closed position as further depicted in FIG. 13.

Figure 13:
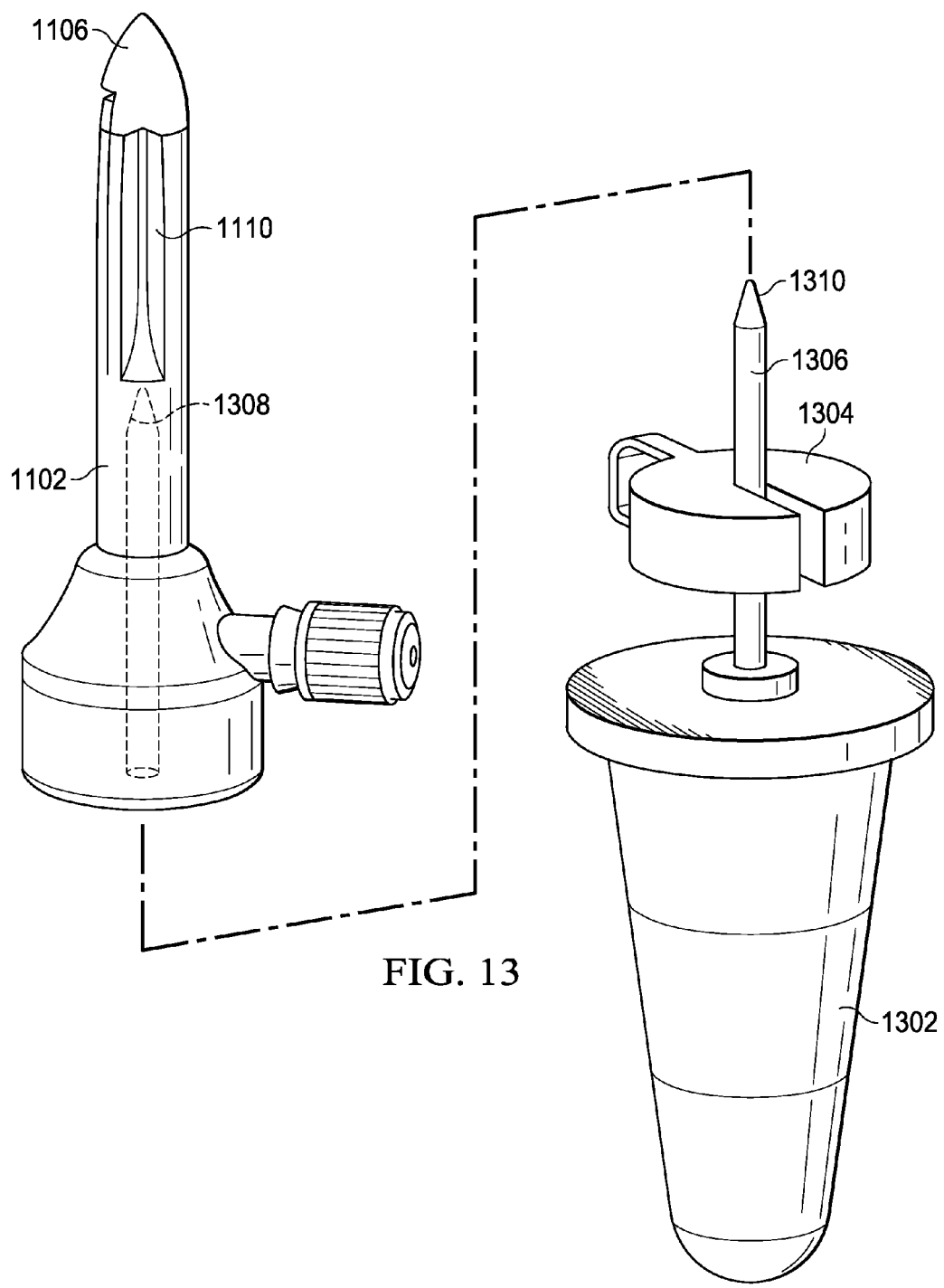
FIG. 13 is a depiction of the alternative embodiment of the cannula invention prior to insertion of the trocar device.

FIG. 13 depicts the additional elements of this embodiment as well as the prepared cannula device. As shown, the embodiment includes a trocar device having a handle (1302) with a shaft member (1306) extending from the proximal end to form a tapered distal end (1308). An anti-plunging device (1304) attaches to the shaft member (1306), and the tapered distal end (1308) is inserted into the proximal end of the cannula device lumen. The anti-plunging device (1304) blocks the shaft member distal end (1308) from advancing past a first position as shown in the figure by hidden lines in the body member (1102). This first position prevents the shaft member distal end (1308) from contacting the corrugated feature (1110) in the fins.

Once assembled, this embodiment may be utilized with a patient by inserting the distal end of the fin into an incision in the patient's skin. Once the body member (1102) is fully inserted, the anti-plunging device (1304) is removed from the shaft (1306) and the trocar is further inserted past the first position to a second position. In the second position, the tapered distal end (1308) contacts the corrugated features (1110), applying force to the fins such that the captured fins are dislodged from beneath the locking feature (1106). The bias pressures of the fins then force the fins to return to the initial outward-bias position, compressing the patient's tissue through which the cannula device was inserted (as in FIG. 19).

FIG. 14 is a proximal end view depiction of an embodiment of the cannula invention highlighting penetrations (also alternatively referred to herein as "cavities") into which a biasing device may be inserted. As shown, the cannula device proximal collar (114) features an additional rectangular biasing device penetration (1402) for accepting an insertable biasing device as depicted in FIG. 16. Each penetration (1402) includes a recessed feature (1404) that reduces the amount that the inserted biasing device protrudes above the surface of the proximal collar (114). The embodiment shown includes a plurality of fins (106), each with penetration that runs from the proximal collar surface to an area beyond the outward bend in the outwardly biased flexible fins (106). In this embodiment in which insertable biasing devices are utilized, it is possible that the biasing forces imparted by the bare flexible fins (106) (no biasing device inserted) can be minimal, which reduces the inward force necessary to converge the fins for insertion of the device into an incision in the skin of a patient.

It is also envisioned that another embodiment may have a plurality of fins with less than all fins having a biasing device penetration. The biasing device penetrations (1402) may be formed by drilling, machining, reaming, or molding the cannula device, or by any other process known in the art that is appropriate for the material utilized for construction of the cannula device. Also, although a rectangular-shaped biasing device penetration is shown, other shapes are envisioned. For example, FIG. 15 is a proximal end view depiction of another embodiment of the cannula invention highlighting penetrations into which a biasing device of an alternate shape may be inserted. The biasing device penetration (1502) in this figure is circular, but one of ordinary skill to which the invention pertains will understand and appreciate that other shapes may be utilized. For example, it is envisioned that the biasing device may utilize a triangular, hexagonal, or octagonal cross section. A recessed feature (1504) is again shown, and is a shape that corresponds to the proximal head of the insertable biasing device. Further, it is also envisioned that multiple penetrations may be formed within a flexible fin (106), thereby allowing a given flexible fin (106) with penetrations to accept one or more insertable biasing devices.

FIGS. 16 and 17 depict two example embodiments of biasing device for the instant invention. FIG. 16A depicts a side view of a rectangular-shaped embodiment of a biasing device, while FIG. 16B depicts a front view of the rectangular-shaped embodiment of the biasing device. Shown is the biasing device (1600) rectangular shaped body (1604) and an attached proximal head (1602). The biasing device features a static bend near the distal end that substantially corresponds to the outwardly biased flexible fin (106) bend into which the biasing device (1600) is to be inserted. The proximal head (1602) provides a feature that allows an operator to apply finger pressure to the device (1600) during insertion and removal. The proximal head (1602) also limits the distance the device (1600) may penetrate into the biasing device penetration (1402/1404). FIG. 17A depicts a side view of a cylindrical-shaped embodiment of a biasing device, while FIG. 17B depicts a front view of the cylindrical-shaped embodiment of the biasing device. The biasing device (1700) cylindrical body (1704) has a circular cross section, with a proximal head (1602) and a static bend near the distal end that substantially corresponds to the outwardly biased flexible fin (106) into which the biasing device (1700) is to be inserted.

Figure 18:
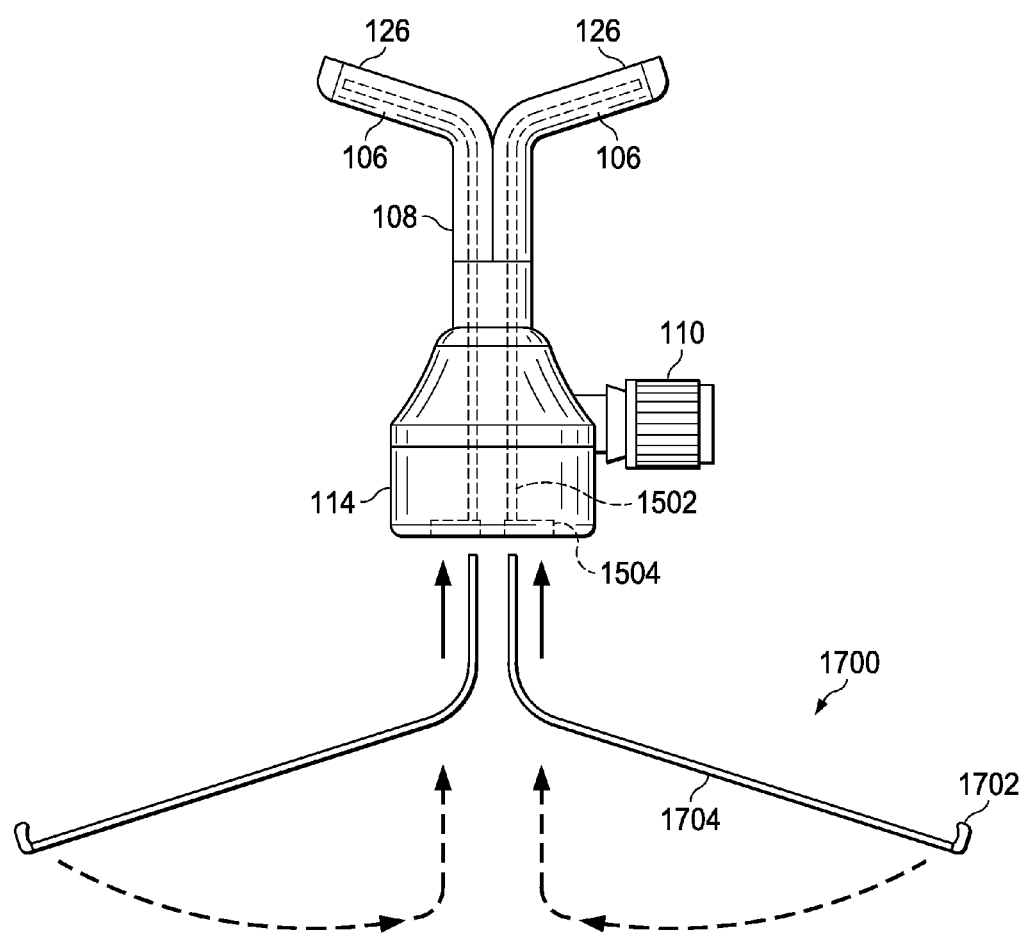
FIG. 18 depicts a side view of an embodiment of the cannula invention highlighting installation of a biasing device.

The cannula device may be prepared by a technician or surgeon prior to use. FIG. 18 is a side view of an embodiment of the cannula invention highlighting installation of the biasing device during device preparation. The cannula device includes biasing device penetrations (1502) —shown in ghosted lines for clarity—extending from the proximal collar (114) surface to substantially the distal tip of the fins (106). The technician or surgeon first converges the fins (106) by finger pressure or trocar and then inserts the distal end of a biasing device (1700) into the penetration (1502) up to the bend and rotates the biasing device body (1704) inward towards the body member (108) lumen while inserting the biasing device (1700) until the proximal head (1702) substantially engages the biasing device recess (1504). Friction between the penetration (1502) wall and the biasing device body (1704) retains the biasing device (1700) or, alternately, a textured body surface may be utilized to cause the biasing device (1700) to be effectively permanently retained within the penetration (1502). Following surgery the biasing device (1700) may be removed from the disposable cannula and sterilized for reuse in another such cannula. Removal of the alloy biasing device (1700) will also allow for proper recycling/disposal of a polymer cannula. Reuse of the biasing device (1700) will also reduce the overall equipment material costs associated with this cannula device.

The cannula device may also be prepared with additional biasing devices (1700) after the cannula device has been inserted into a patient. In such an instance the surgeon, following insertion of the lumen into an incision in the patient's skin, allows the distal tips of the fins (106) to splay outward as the biasing devices (1700) are inserted as before. Thus, the outward biasing force of the fins (106) may be adjusted inside the patient if necessary. For example, if the retractable cannula fin (106) outward biasing pressure is sufficient without the biasing devices (1700), the biasing devices (1700) may be omitted from the procedure. However, if the patient has an excess of tissue to compress and the fin (106) pressure is inadequate to do so, then one or more biasing devices (1700) may be inserted as above. Further, biasing devices (1700) of differing biasing force (for example, by using different material gauges, cross sectional shapes, compositions, or the like or some combination thereof) may be utilized to allow fine-tuning of the fin (106) compressive force.

Figure 19:
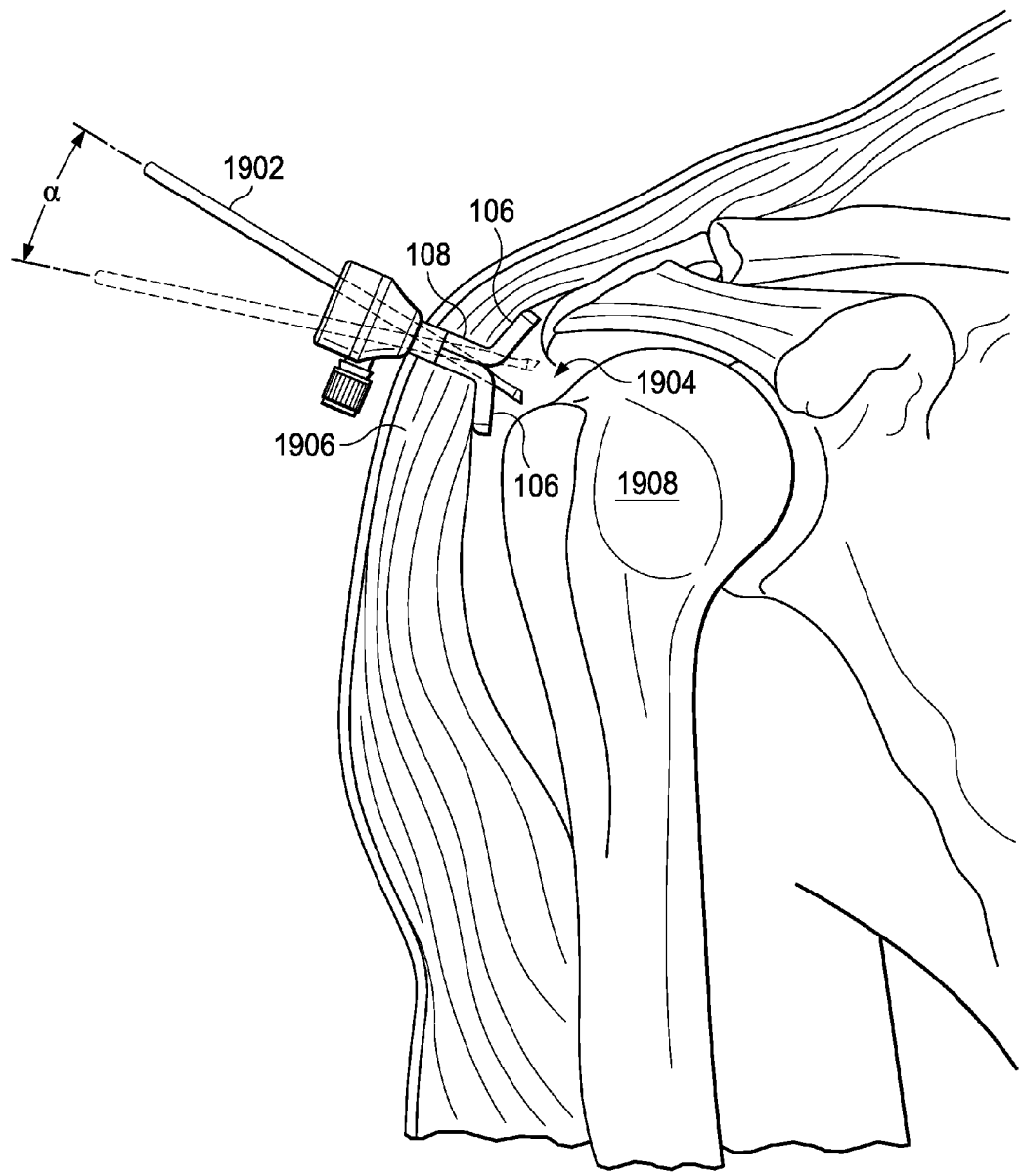
FIG. 19 depicts a cutaway view of an embodiment of the invention in use during shoulder surgery.

Once inside a patient, the trocar is removed from the cannula device and the fins naturally return to their outwardly-biased position. FIG. 19 depicts such an event. As shown, the body member (108) forms a port in the patient's skin and outer tissue (1906) through which surgical instruments (1902) may pass. The outwardly biased flexible fins (106) of the cannula device exert pressure on the tissue (1906) and assist the surgeon in compressing the tissue (1906) to allow for a greater working cavity (1904) and exposure of the surgery site (1908). Because of the compressive effect of the flexible fins (106) on the tissue (1906), the length of the body member (108) may be made relatively short compared to conventional cannula devices. This shortened body member (108) results in a shortened lumen length that, consequently, allows a greater working angle (shown on the figure as the Greek letter "a") for the surgeon's tools (1902), which improves the surgeon's access to the surgery site and reduces the need for physical manipulation of the cannula during surgery. When surgery is complete, the cannula device may be removed by reinserting the trocar device into the lumen such that the trocar raised members engage the slots in the fins and the fins move inward once more. The cannula device may then be withdrawn from the patient with minimal tissue damage. Although the present embodiment is described in use during shoulder arthroscopy, one of ordinary skill will understand that the device may be employed in essentially any arthroscopic, laparoscopic, or other types of endoscopic surgery requiring the surgeon to establish a working port in the tissue of a patient. Moreover, it should be noted that alternate embodiments of the cannula invention may be utilized to perform endoscopic surgery on subjects other than humans such as, for example, animals such as dogs, cats and livestock. Those of ordinary skill in the art will recognize that the dimensions of the cannula invention will require modification depending upon the anatomical structures of the particular subject of the surgery in which the invention is utilized, as wells as the type of endoscopic surgery being performed.

Figure 20:
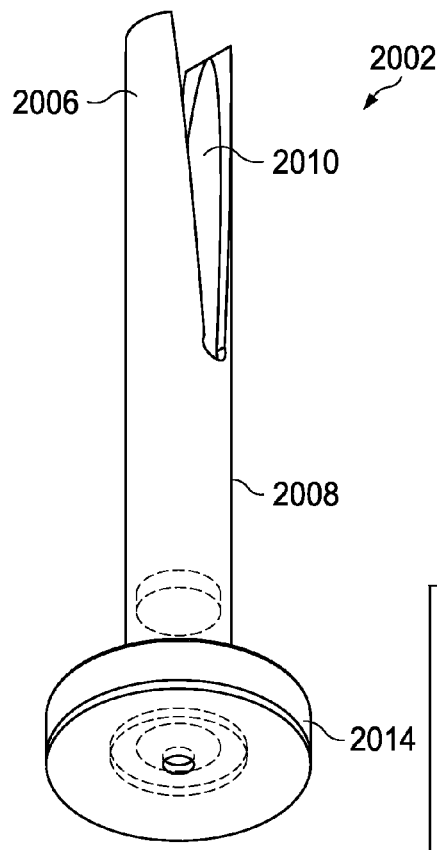
FIG. 20 a perspective view of a further alternate embodiment of a cannula device having cavities formed within to accept insertion of shafts of a biasing device.
Figure 22:
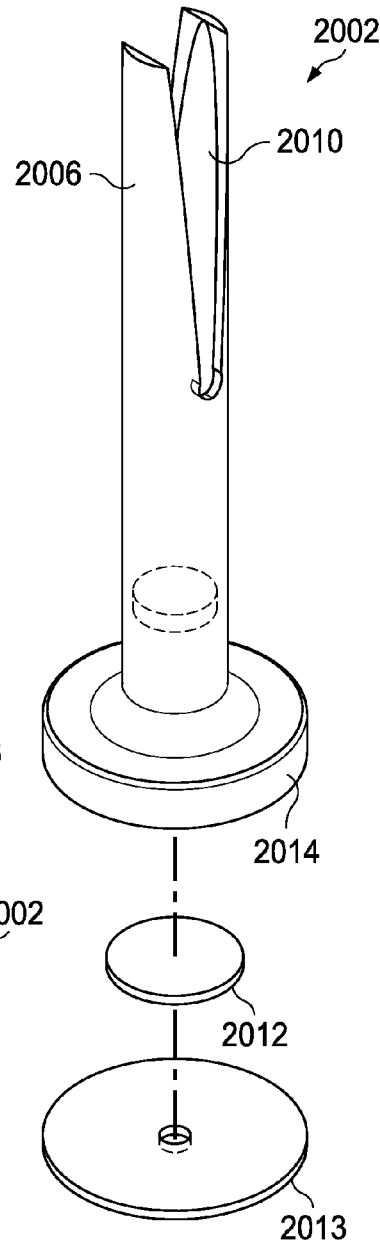
FIG. 22 depicts an exploded view of the alternate embodiment of the cannula device shown in FIG. 20 and FIG. 21.
Figure 21:
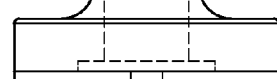
FIG. 21 depicts a side view of the further alternate embodiment of the cannula device as shown in FIG. 20.

Referring now to FIG. 20, a perspective view of a further alternate embodiment of a cannula device (2002). The cannula device (2002) comprises a body member (2008), two fins (2006) and a proximal collar (2014). Longitudinal cavities (2010) formed into the fins (2006) provide a passage through which a biasing device (not shown) may be embedded. While the biasing devices of the preferred embodiments described herein are removably insertable into the cannula device, it is contemplated that alternate embodiments may include biasing devices that are integrally embedded into the cannula device. The proximal collar (2014) retains discs used to provide a seal through which surgical instruments may pass. Referring now to FIG. 21, a side view of the further alternate embodiment of the cannula device (2002) as shown in FIG. 20. The cannula (2002) is constructed of medical grade polymer and includes flexible fins (2006) that are neutral with respect to their outward and inward biasing pressure. In even further alternate embodiments, the cannula may be at least partially composed of polymers constructed to provide the fins with an outward biasing pressure at normal temperatures as has been described with respect to the embodiments of the cannula discussed above. Referring now to FIG. 22, an exploded view of the alternate embodiment of the cannula device (2002) shown in FIG. 20 and FIG. 21. A silicone rear gate seal (2012) is attached to the proximal collar (2014) and provides a retaining structure to secure the one or more insertable biasing devices (not shown) within the cannula device (2002) during use. A silicone spacer (2013) is attached to the proximal collar (2014) at a location proximal to the silicone rear gate seal (2012).

Figure 23:
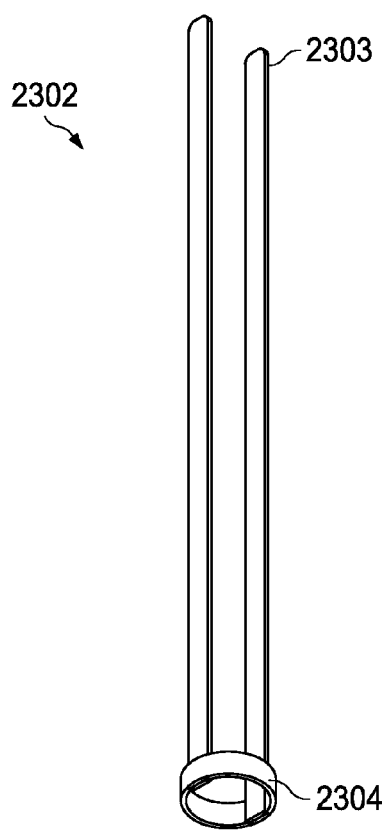
FIG. 23 depicts a perspective view of an alternate embodiment of a biasing device for use insertion into the alternate embodiments of the cannula device shown in FIGS. 20, 21 and 22.

Referring now to FIG. 23, a perspective view of an alternate embodiment of a biasing device (2302) for use in the alternate embodiments of the cannula device shown in FIGS. 20, 21 and 22. The biasing device (2302) is comprised of two elongated shafts (2303) joined at their respective proximal ends by a circular collar (2304). The shafts of the biasing devices shown in FIG. 23 are generally rectangular in the cross-section. However, as has been noted above, alternate embodiments of biasing devices may include shafts having cross sections of various shapes. The biasing device is composed at least partially of a shape memory alloy such as Nitinol, allowing a user to "train" the biasing devices to take on a desired form.

Figure 24:
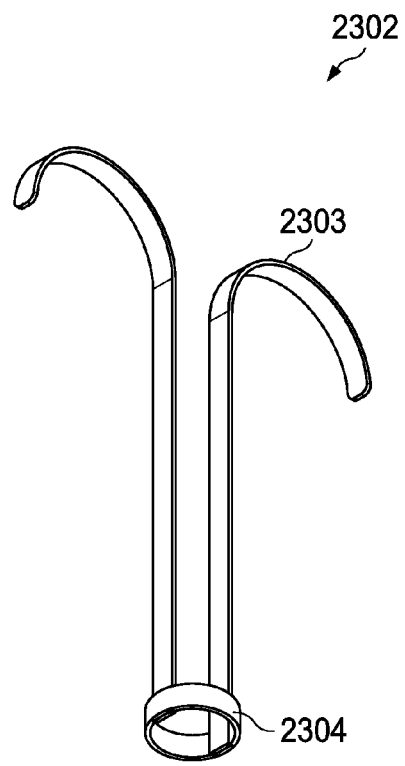
FIG. 24 depicts a perspective view of the alternate embodiment of the biasing device shown in FIG. 23, when such device is in a phase wherein distal portions of the biasing device's shafts are flexed outward.

Referring now to FIG. 24, a perspective view of the alternate embodiment of the biasing device shown in FIG. 23, when such device is in a phase wherein distal portions of the biasing device's shafts are flexed outward. The biasing devices may be composed of materials and "trained" to provide for such outward flexing at desired temperatures. For example, the biasing device may be trained to exhibit such outward flexing upon encountering temperature approximating typical human body temperatures. As previously discussed, biasing devices composed of shape memory alloy(s) may be electrically activated to exhibit such flexing in amounts corresponding to electrical current passed through such biasing devices.

Figure 25:
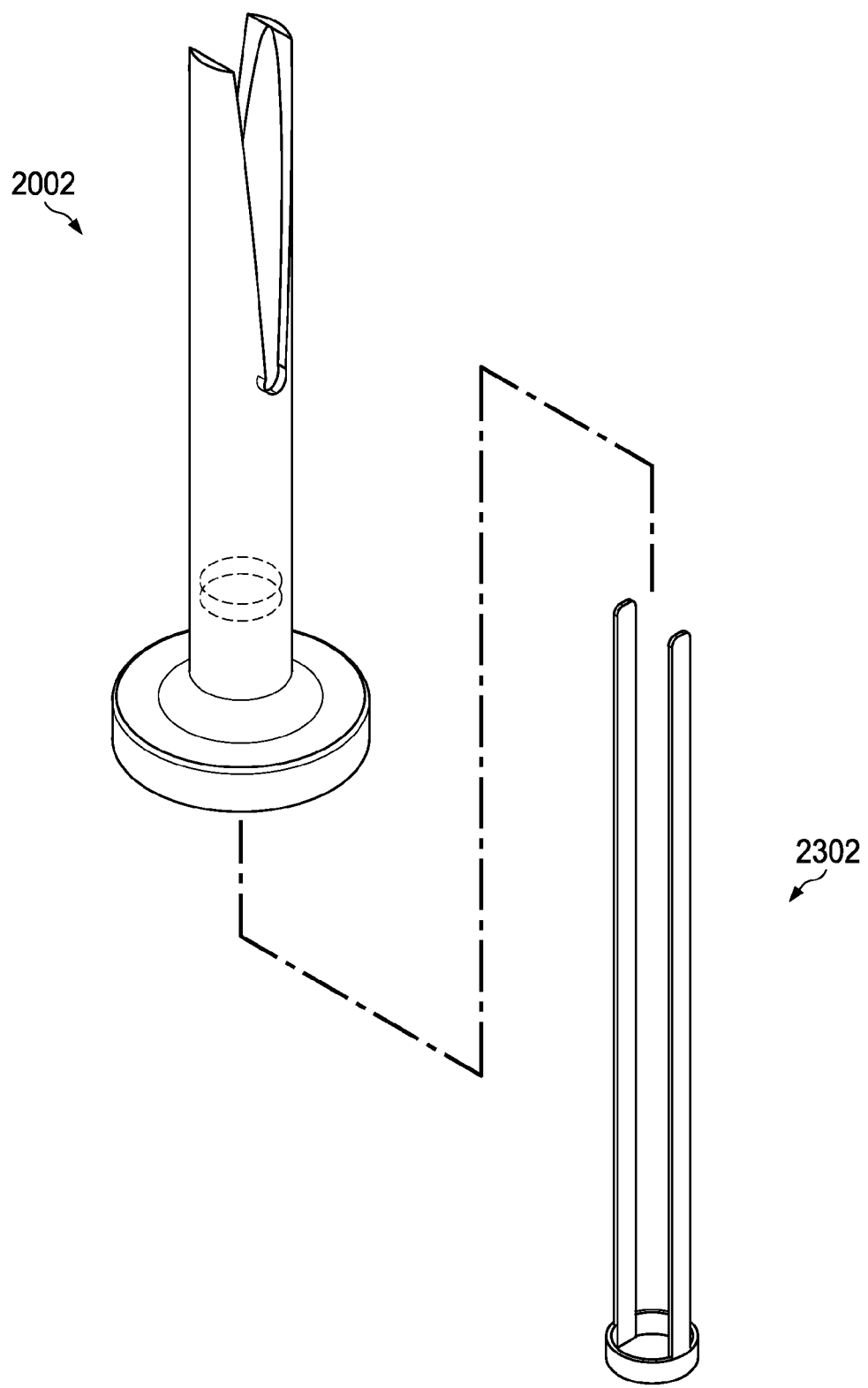
FIG. 25 depicts perspective views of the alternate embodiments of the cannula device and biasing device as shown in FIG. 20 and FIG. 23, respectively.

Referring now to FIG. 25, perspective views of the alternate embodiments of the cannula device (2002) and biasing device (2302) as shown in FIG. 20 and FIG. 23, respectively. Both the cannula device (2002) and biasing device (2302) are configured to mate with one another, allowing a user to insert the biasing device into the cannula device through cavity openings in the cannula device formed into the proximal collar (similar to the penetrations (1504) shown at FIG. 15 and FIG. 18).

Figure 26:
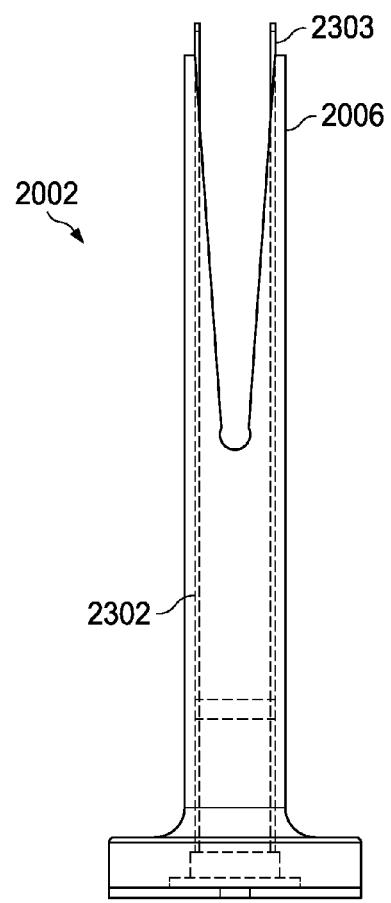
FIG. 26 depicts a side view of the alternate embodiment of the cannula device having an alternate embodiment of a biasing device (shown in broken lines) embedded within cavities formed into the cannula device.

Now referring to FIG. 26, a side view of the alternate embodiment of the cannula device (2002) having an alternate embodiment of a biasing device (2002) (shown in broken lines) embedded within cavities (or "penetrations") formed into the cannula device (2002). The distal ends (2303) of the shafts of the biasing device protrude beyond the distal ends of the cannula device such that when the fins (2006) are released from the trocar device and flex outward, the distal ends (2303) of the biasing device will retreat into the cannula (not protrude as shown in FIG. 26). Further, the protruding nature of the distal ends (2303) of the shafts of the biasing device also provide a structure which may be removably secured to the distal end of a trocar device shaft (via a notch formed onto the distal head of the trocar shaft, said notch shaped to receive and removably secure the distal end of the biasing device shaft), thus keeping the biasing shafts and cannula fins from prematurely flexing outwardly. When activated, through heat, electrical current, or other means, the shafts of the biasing device are configured to flex outwardly, causing the fins (2006) of the cannula to also flex outwardly. Such outward flexing, when the cannula is inserted into the surgical site, assists the surgeon in both compressing the patient's tissue, and further providing a larger working cavity.

Figure 27:
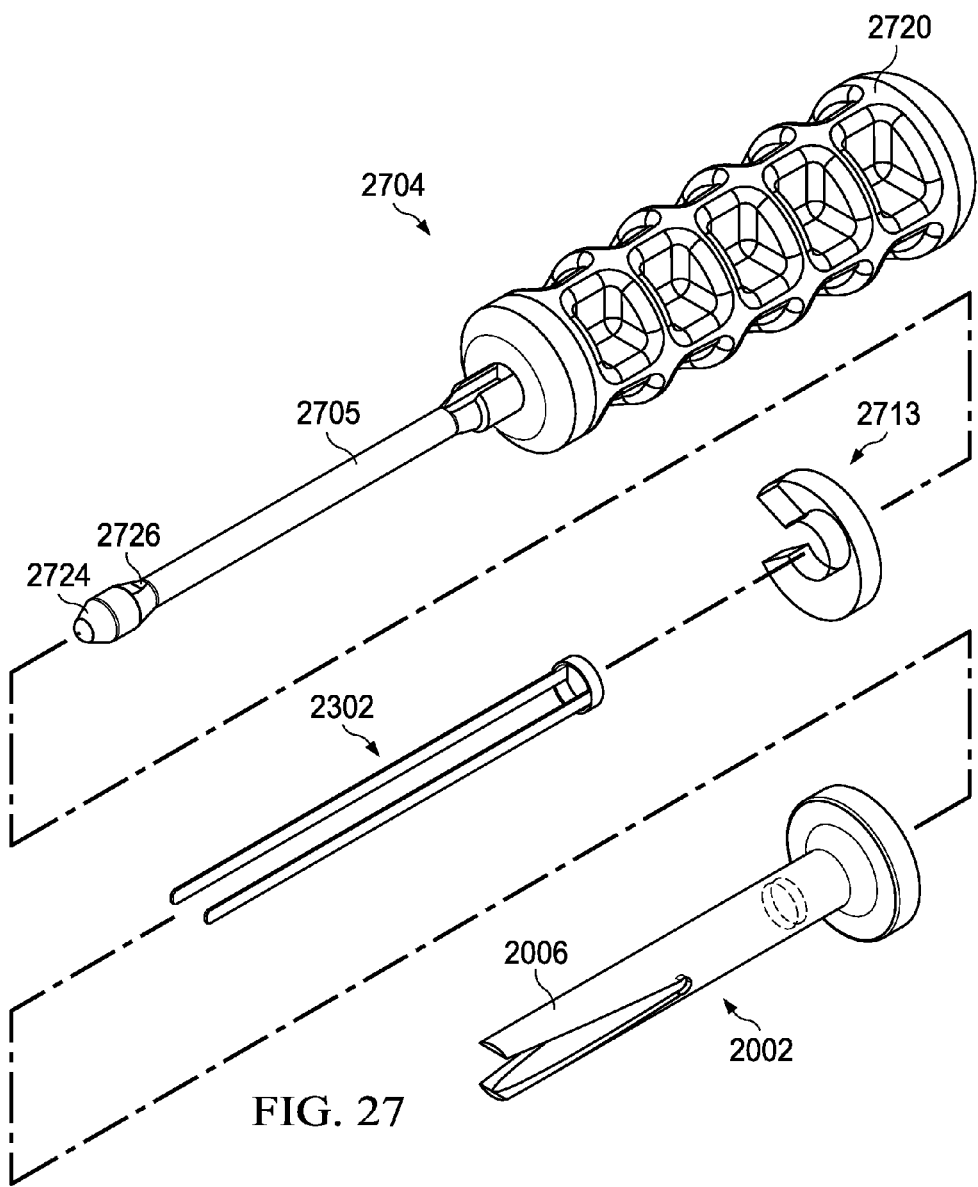
FIG. 27 depicts an exploded view of an alternate embodiment of the cannula device and biasing device as shown in FIG. 26, along with an alternate embodiment of a trocar device for use therewith.

Referring now to FIG. 27, an exploded view of an alternate embodiment of the cannula device (2002) and biasing device (2302) as shown in FIG. 26, along with an alternate embodiment of a trocar device (2704) for use therewith. The trocar device (2704) serves the purpose of both providing a mechanism for physically placing the cannula device (with embedded biasing device) at the surgical site, and also serves to release the biasing device from the inward pressure applied by the shaft (2705) of the trocar device. Notches (2726) formed on the distal end (2724) of the trocar device shaft (2705) are shaped to receive and removably secure the distal ends of the shafts of the biasing device (2302). The distal ends of the biasing device shaft may be inserted into the notches (2726) formed on opposite sides of the distal end of the trocar device. When inserted into the notches, the distal ends of the biasing devices are prevented from flexing outwardly. The trocar device may be constructed of any number of polymers or other materials having rigid or semi-rigid properties. A "c" shaped spacer (2713) is shaped and sized to be removably secured around the proximal end of the trocar device shaft (2705), such that it is located between the distal end of the trocar device handle (2720) and the proximal collar of the cannula device when the trocar device is attached to said cannula. The spacer (2713) serves to prevent the premature deployment of the biasing device shafts and cannula fins until the time desired by the surgical team. When the spacer (2713) is removed from the space between the distal end of the trocar device handle (2720) and the proximal collar of the cannula, the trocar device may then be moved in a distal direction (generally towards the patient when the cannula has been inserted into a patient), decreasing the gap between said handle and the proximal collar, such that the distal ends of the biasing device shafts are disengaged from the notches (2726), allowing said shafts and the cannula fins to flex outwardly. In this manner, a surgeon may deploy the fins of the cannula at a desired time during a surgical procedure.

Figure 28:
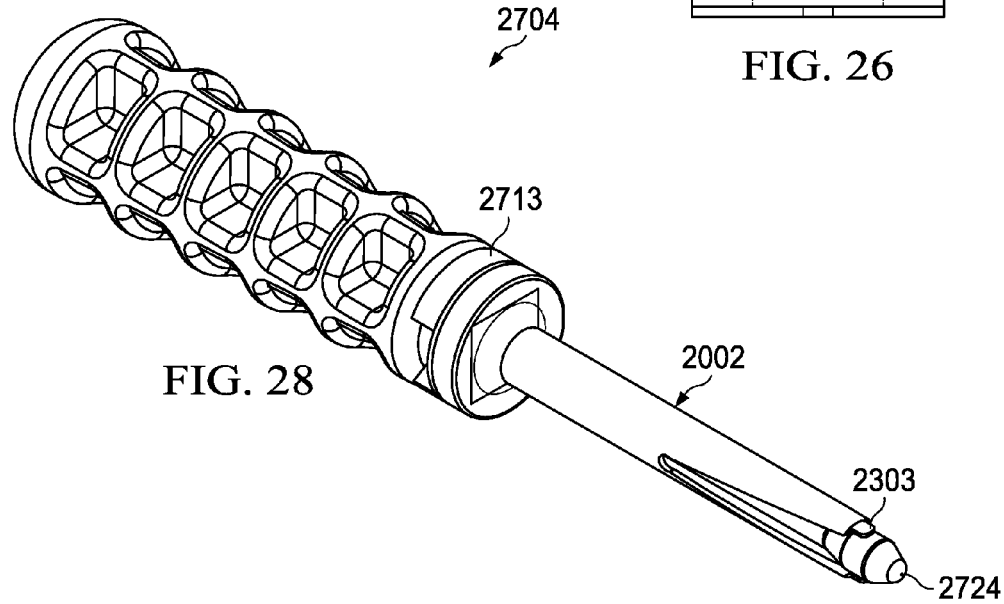
FIG. 28 depicts a perspective view of the alternate embodiments on the cannula device (2002) and trocar device (2704) shown in FIG. 27.

Referring now to FIG. 28, a perspective view of the alternate embodiments on the cannula device (2002) and trocar device (2704) shown in FIG. 27. The shaft of the trocar device (2704) is shown inserted into an opening (not shown) in the proximal end of the cannula device such that the distal end (2724) of the trocar shaft protrudes from the distal end of the cannula device. The distal ends (2303) of the biasing device likewise protrude beyond the end of the cannula device. The configuration of the cannula device and trocar device shown in FIG. 28 demonstrate the appearance of such devices prior to insertion into a patient. It should be noted that the distal ends of the biasing device shafts are not shown inserted into the notches (2726) in the drawing shown at FIG. 28. The "c" shaped spacer (2713) is removably secured between the distal end of the trocar device handle and the proximal collar of the cannula. Following completion of the surgery, the biasing device may be returned to its inward phase (through use of thermal or electrical control, or through use of the trocar device) and the trocar device may be used to remove the cannula from the surgical site. The cannula may alternatively be removed without use of a trocar device, utilizing methods discussed above or as known in the art.

Figure 29:
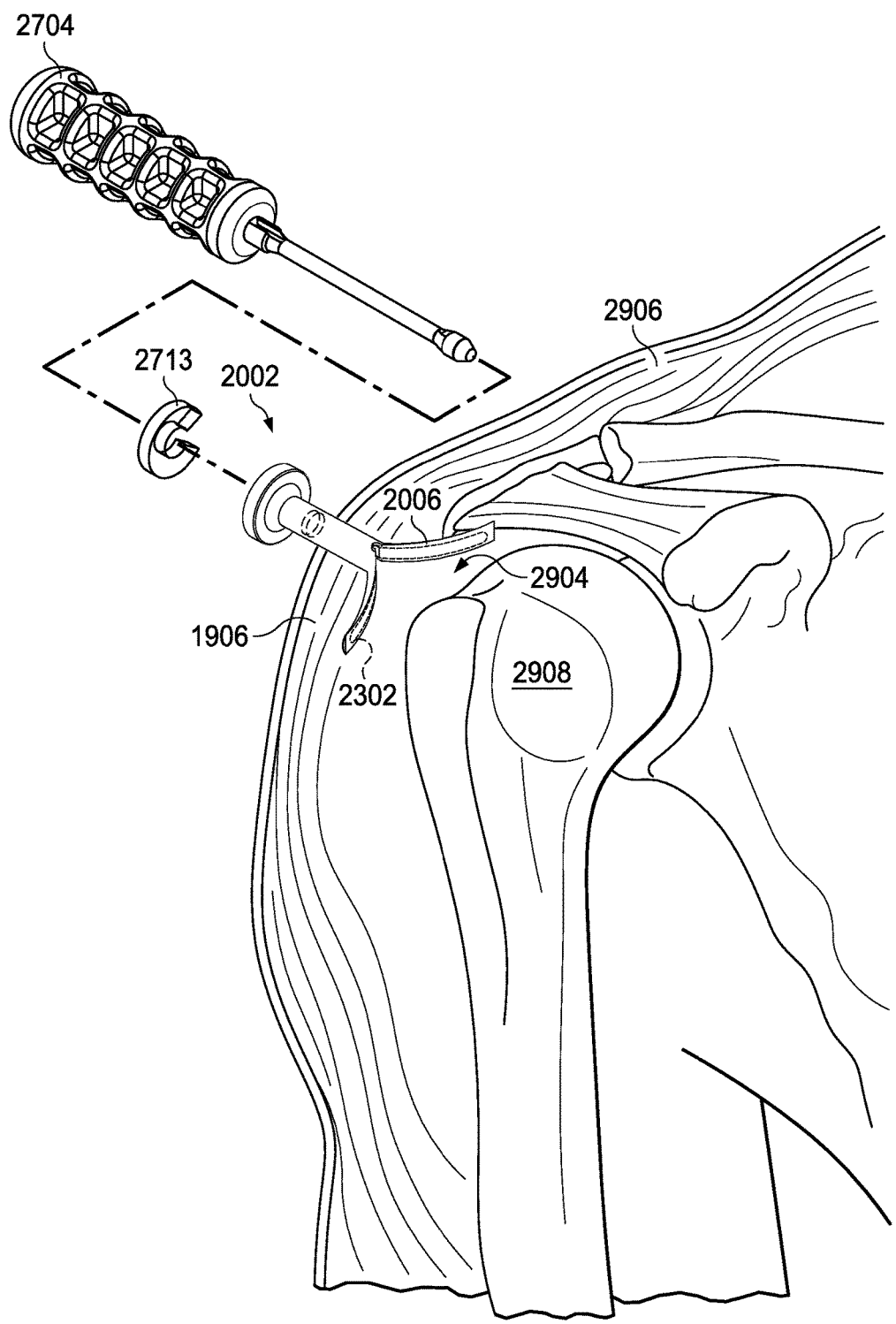
FIG. 29 depicts a cutaway view of the alternate embodiment of the cannula device and trocar device as shown in FIG. 28, in use during shoulder surgery.

Referring now to FIG. 29, showing a cutaway view of the alternate embodiment of the cannula device and trocar device as shown in FIG. 28, in use during shoulder (2906) surgery. The cannula device (2002) has been inserted into the patient's shoulder through use of the trocar device (2704). At the appropriate time, the surgical team may remove the "c" shaped spacer (2713) from the trocar device, allowing the trocar device to be moved distally toward the patient. As the cannula device will remain generally stationary during such movement of the trocar device, the distal ends of the biasing device shafts (2302) will slide out of the notches securing them to the end of the trocar device shaft. Once the distal ends of the biasing device shafts are no longer secured in the notches, said shafts (2302) and the cannula fins (2006) will be free to flex in an outward direction as shown in FIG. 29. The flexible fins (2006) of the cannula device assist the surgical team in compressing the patient's tissue (1906) so that a greater working cavity (2904) is formed, providing better exposure of the surgery site (2908). The outward flexing of the cannula fins also works to put increased pressure on the ports and other cavities inside the cannula. Such increased pressure on the ports and other cavities inside the cannula device aids in creating tighter seals between the cannula device and other surgical instruments passing through the cannula device, leading to less fluid leakage during surgery.

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes that come within the meaning and range of equivalency of the claims are embraced therein. Further, the recitation of method steps does not denote a particular sequence for execution of the steps. Such method steps may therefore be performed in a sequence other than that recited unless the particular claim expressly states otherwise.

I claim:

1. A cannula for surgical procedures, the cannula comprising:
    a body member having an inner wall forming a lumen along at least a proximal portion of a length of said body member to form a port for a surgical tool, said inner wall and an outer wall of said body member being split to form branches at a distal end of said lumen so as to form a plurality of flexible fins,
    wherein a cavity is disposed within each of said plurality of flexible fins,
    wherein one biasing device is embedded within each of said cavities.

2. The cannula of claim 1, wherein a distal tip of each biasing device protrudes from a distal end of the respective cavities in which said biasing device is embedded within.

3. The cannula of claim 1, wherein each biasing device is insertable into one of said the respective cavities in which said biasing device is embedded within.

4. The cannula of claim 3, wherein each biasing device comprises a proximal head for controlling depth of insertion of each biasing device.

5. The cannula of claim 3, wherein each biasing device is also reusable.

6. The cannula of claim 3, wherein each biasing device comprises a textured feature on at least a portion of a surface of each said biasing device.

7. The cannula of claim 1, wherein each biasing device comprises a polymer.

8. The cannula of claim 1, wherein each biasing device comprises a shape memory alloy.

9. The cannula of claim 1, wherein a proximal end of each biasing device is secured to a proximal end of said body member.

* * * * *